United States Patent [19]
Krishnan et al.

[11] Patent Number: 4,463,163
[45] Date of Patent: Jul. 31, 1984

[54] POLYCARBONATE FROM 4,4'-BIS(4-HYDROXYPHENYL THIO)BIPHENYLS

[75] Inventors: Sivaram Krishnan, Moers, Fed. Rep. of Germany; John R. Sanderson, Austin, Tex.

[73] Assignee: Mobay Chemical Corporation, Pittsburgh, Pa.

[21] Appl. No.: 383,893

[22] Filed: Jun. 1, 1982

[51] Int. Cl.$^3$ .............................................. C08G 63/62
[52] U.S. Cl. .................................... 528/196; 528/204
[58] Field of Search ............................... 528/196, 204

[56] References Cited

U.S. PATENT DOCUMENTS 3,751,483  8/1973  Cisney .................................. 528/196

Primary Examiner—Harold D. Anderson
Attorney, Agent, or Firm—Gene Harsh; Lawrence S. Pope; Aron Preis

[57] ABSTRACT

The present invention relates to the novel monomer 4,4'-bis(4-hydroxyphenyl thio)biphenyl, to a process for its production and to its use in the preparation of polycarbonates, polyurethanes, polyesters, polysulfones and polyethers which polymer resins are useful in the preparation of films, fibers and molded parts.

4 Claims, No Drawings

POLYCARBONATE FROM 4,4'-BIS(4-HYDROXYPHENYL THIO)BIPHENYLS

FIELD OF THE INVENTION

This invention is directed to monomers and more particularly to 4,4'-bis(4-hydroxyphenyl thio)biphenyls.

SUMMARY OF THE INVENTION

The present invention is directed to novel monomers identified as 4,4'-bis(4-hydroxyphenyl thio)biphenyls of the structural formula

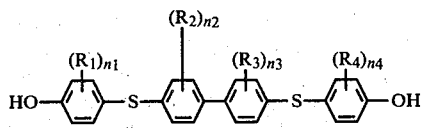

wherein $R_1$, $R_2$, $R_3$ and $R_4$, which may be the same or different, are $C_1$-$C_4$-alkyl, Cl or Br, and $n_1$, $n_2$, $n_3$ and $n_4$, which may be the same or different, are 0, 1, or 2, as well as to a process for their synthesis and their use in the preparation of certain polymeric resins.

DETAILED DESCRIPTION OF THE INVENTION

A route suitable for the synthesis of the generic 4,4'-bis(4-hydroxyphenyl thio)bisphenyls is illustrated by the following general reaction scheme for the synthesis of 4,4'-bis(4-hydroxyphenyl thio)biphenyl, the preferred monomer of the present invention:

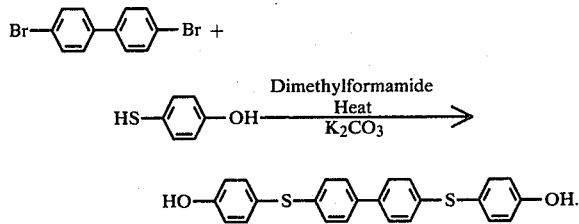

As indicated in the above reaction scheme, 4,4'-dibromobiphenyl is reacted with 4-mercaptophenol in the presence of potassium carbonate and dimethylformamide to produce the 4,4'-bis(4-hydroxyphenyl thio)biphenyl of the present invention. The resulting monomer is recovered as a precipitate and is then separated and dried.

The generic 4,4'-bis(4-hydroxyphenyl thio)biphenyls of the invention are useful as monomers or as one of the comonomers in the synthesis of polycarbonates, polyurethanes, polyesters, polysulfones, polyethers and other polymers. The corresponding comonomer in the synthesis of copolycarbonates may be a dihydric phenol selected from the group consisting of 2,2-bis(4-hydroxyphenyl)-propane (bisphenol A); 2,4'-dihydroxydiphenylmethane; bis-(2-hydroxyphenyl)-methane; bis-(4-hydroxyphenyl)-methane; bis-(4-hydroxy-5-nitrophenyl)-methane; bis-(4-hydroxy-2,6-dimethyl-3-methoxyphenyl)-methane; 1,1-bis(4-hydroxyphenyl)-ethane; 1,2-bis-(4-hydroxyphenyl)-ethane; 1,1-bis-(4-hydroxy-2-chlorophenyl)-ethane; 1,1-bis-(2,5-dimethyl-4-hydroxyphenyl)-ethane; 1,3-bis-(3-methyl-4-hydroxyphenyl)-propane; 2,2-bis-(3-phenyl-4-hydroxyphenyl)-propane; 2,2-bis-(3-isopropyl-4-hydroxyphenyl)-propane; 2,2-bis-(4-hydroxynaphthyl)-propane; 2,2-bis-(4-hydroxyphenyl)-pentane; 3,3-bis-(4-hydroxyphenyl)-pentane; 2,2-bis-(4-hydroxyphenyl)-heptane; bis-(4-hydroxyphenyl)-phenylmethane; bis-(4-hydroxyphenyl)-cyclohexylmethane; 1,2-bis-(4-hydroxyphenyl)-12-bis-(phenyl)-ethane; 2,2-bis-(4-hydroxyphenyl)-1,3-bis-(phenyl)-propane; and 2,2-bis-(4-hydroxyphenyl)-1-phenylpropane. Such polymers are generally useful in films, fibers, injection molded parts, extruded parts and molded parts, blow molded articles and coatings.

Such polycarbonates are produced using the novel monomers of the invention by well-known methods, such as disclosed in U.S. Pat. Nos. 2,964,794; 2,970,131; 2,991,237; 2,999,835; 2,999,846; 3,028,365; 3,153,008; 3,187,065; 3,215,668; and 3,248,414, all incorporated herein by reference and in the monograph H. Schnell, *Chemistry and Physics of Polycarbonates*, Interscience Publishers, New York, N.Y., 1964. Preferably, such polycarbonates may be produced by the well-known melt polymerization technique taught in the above references.

Such polyurethanes are produced using the novel monomers of the invention by well-known methods, such as disclosed in U.S. Pat. Nos. 2,266,777; 2,284,637; 2,284,296; 2,511,544, all incorporated herein by reference and in the text *Polyurethanes: Chemistry and Technology*, Vol. 1, J. H. Saunders and K. C. Frisch, Interscience Publishers, New York, N.Y., 1964.

Such polyesters are produced using the novel monomers of the invention by well-known methods, such as disclosed in U.S. Pat. Nos. 2,980,650; 3,185,668; 3,185,670 and 3,268,482, all incorporated herein by reference, and in the text *Polyesters (two parts)*, edited by Norman G. Gaylord, Interscience Publishers, New York, 1962.

Such polysulfones are produced using the novel monomers of the invention by well-known methods, such as disclosed in U.S. Pat. Nos. 3,236,808; 3,236,809; 3,409,599 and 3,742,087, all incorporated herein by reference.

Such polyethers are produced using the novel monomers of the invention by well-known methods, such as disclosed in U.S. Pat. Nos. 1,922,459; 2,253,723; 2,991,313 and 3,651,151, all incorporated herein by reference, and in the text *Polyethers (three parts)*, edited by Norman G. Gaylord, Interscience Publishers, New York, 1962.

The invention will further be illustrated, but is not intended to be limited, by the following example.

EXAMPLE

Preparation of 4,4'-dibromobiphenyl

Biphenyl (15.4 g, 0.10 mol), bromine (21.8 ml, 0.40 mol) and 200 ml of glacial acetic acid were placed in a flask equipped with a stirrer, heating mantle, and condenser and refluxed for 17 hours. The reaction mixture was cooled to 20°-25° C. and a white solid collected, washed with water and air dried to yield 24.5 g (79% yield) of 4,4'-dibromobiphenyl (mp 162°-165° C.).

Preparation of 4,4'-bis(4-hydroxyphenyl thio)biphenyl (HPSB)

Potassium carbonate (75.9 g, 0.55 mol) was charged to a 2 liter flask equipped with a stirrer, condenser, dropping funnel, thermometer and nitrogen purge. Dimethylformamide (200 ml) was added and the solution heated to 80°-90° C. 4-mercaptophenol (69.3 g, 0.55 mol) in 200 ml of dimethylformamide was added to the stirred reaction mixture over one hour. The reaction mixture was maintained at 100°-110° C. for two hours. Solid 4,4'-dibromobiphenyl (78 g, 0.25 mol) was then added over one hour. The reaction mixture was refluxed for 18 hours, cooled to room temperature, and poured into 10% HCl. The white to yellow solid was collected with suction and washed with water. The solid was treated with 5-10% NaOH and filtered once more with suction. The mother liquor was acidified to pH≈2 and the solid collected and recrystallized from chlorobenzene/methanol. A 34% yield of pure HPSB was obtained having a melting point of 214°-217° C.

Analysis of $C_{24}H_{18}O_2S_2(\%)$—Calculated: C, 71.64; H, 4.47; S, 15.92. Determined: C, 71.76; H, 4.61; S, 15.73.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing an aromatic copolycarbonate resin comprising reacting a monomer of the structural formula

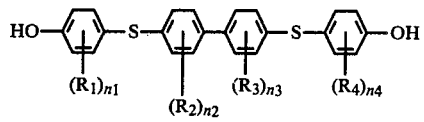

wherein $R_1$, $R_2$, $R_3$ and $R_4$ independently are $C_1$-$C_4$-alkyl, chlorine or bromine and $n_1$, $n_2$, $n_3$ and $n_4$, independently are 0, 1 or 2, with a member selected from the group consisting of carbonyl bromide, phosgene, bis-chloroformic ester of said monomer and diaryl carbonate.

2. A process for preparing an aromatic copolycarbonate resin comprising reacting a comonomer of the structural formula

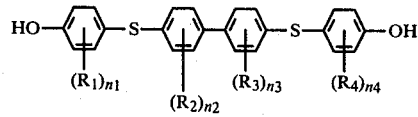

wherein $R_1$-$R_4$ independently are $C_1$-$C_4$ alkyl, chlorine or bromine and $n_1$-$n_4$ independently are 0, 1 or 2 with at least one dihydric phenol selected from the group consisting of 2,2-bis(4-hydroxyphenyl)-propane (bisphenol A); 2,4'-dihydroxydiphenylmethane; bis-(2-hydroxyphenyl)-methane; bis-(4-hydroxyphenyl)-methane; bis-(4-hydroxy-5-nitrophenyl)-methane; bis-(4-hydroxy-2,6-dimethyl-3-methoxyphenyl)-methane; 1,1-bis(4-hydroxyphenyl)-ethane; 1,2-bis-(4-hydroxyphenyl)-ethane; 1,1-bis-(4-hydroxy-2-chlorophenyl)-ethane; 1,1-bis-(2,5-dimethyl-4-hydroxyphenyl)-ethane; 1,3-bis-(3-methyl-4-hydroxyphenyl)-propane; 2,2-bis-(3-phenyl-4-hydroxyphenyl)-propane; 2,2-bis-(3-isopropyl-4-hydroxyphenyl)-propane; 2,2-bis-(4-hydroxynaphthyl)-propane; 2,2-bis-(4-hydroxyphenyl)-pentane; 3,3-bis-(4-hydroxyphenyl)-pentane; 2,2-bis-(4-hydroxyphenyl)-heptane; bis-(4-hydroxyphenyl)-phenylmethane; bis-(4-hydroxyphenyl)-cyclohexylmethane; 1,2-bis-(4-hydroxyphenyl)-2,3-bis-(phenyl)-ethane; 2,2-bis-(4-hydroxyphenyl)-1,2-bis-(phenyl)-ethane; and 2,2-bis-(4-hydroxyphenyl)-1-phenylpropane; and with a member selected from the group consisting of carbonyl bromide, phosgene and bis-chloroformic ester of said comonomer or said dihydric phenol and a diaryl carbonate.

3. The process of claim 2 wherein said dihydric phenol is bisphenol-A.

4. The copolycarbonate prepared in accordance with the process of claim 2.

* * * * *